US00PP10179P

United States Patent [19]

Glaser

[11] Patent Number: Plant 10,179

[45] Date of Patent: Jan. 6, 1998

[54] AZALEA PLANT NAMED KOMET

[76] Inventor: Karl Glaser, Alte Strasse 9, D-64832 Babenhausen, Germany

[21] Appl. No.: 651,713

[22] Filed: May 22, 1996

[51] Int. Cl.[6] ..... A01H 5/00

[52] U.S. Cl. ..... Plt./55

[58] Field of Search ..... Plt./55

[56] References Cited

U.S. PATENT DOCUMENTS

P.P. 1,157 12/1952 Brooks ..... Plt./55

*Primary Examiner*—James R. Feyrer

*Assistant Examiner*—Melissa L. Kimball

[57] ABSTRACT

An azalea plant named Komet particularly characterized by its evergreen foliage, double flower form, white flower color with dark salmon flecks and occasional stripes, free branching, compact semi-upright plant habit, uniform flowering response in a year round controlled program, and by its good tolerance and keeping quality.

1 Drawing Sheet

The present invention comprises a new and distinct cultivar of Azalea, a greenhouse forcing type, hereinafter referred to as Komet.

Komet, identified as US during the selection process, originated from a planned cross hybridization between two selected breeding lines in a controlled breeding program in Babenhausen, Germany by the inventor Karl Glaser.

The female, or seed parent of Komet is an unnamed seedling with large pink single shaped flowers, a round habit, and dark green foliage. The male or pollen parent is a unnamed seedling with red funnel-shaped flowers, round growth habit, and medium green foliage.

Komet was discovered and selected as one flowering plant within the progeny of the stated cross by the inventor Karl Glaser in January 1982 in Babenhausen, Germany.

The first asexual reproduction of Komet was accomplished when vegetative cuttings were taken from the initial selection in April 1982, in Babenhausen, Germany, by technicians working under formulations established and supervised by Karl Glaser.

Horticultural examination of controlled flowerings of successive generations of plants derived from cuttings taken from the original selection has shown that the unique combination of characeristics as herein disclosed for Komet are fixed and retained through successive generations of asexual reproduction.

Komet has not been observed under all possible environmental conditions. The phenotype may vary significantly with variations in environment such as temperature, light intensity and day length, without, however, any variance in the genotpe.

The following observations, measurements and comparisions describe plants that were grown in Salinas, Calif. in a controlled greenhouse environment and following a commercial schedule.

The following traits have been repeatedly observed and are determined to be basic characteristics of Komet, which in combination distinguish this azalea as a new and distinct cultivar:

1. White flower color (155D), with dark salmon flecks and occasional stripes upon opening, fading to an off white color (155B) as flowers age.
2. Double flowers, with the flowers ranging from 7.0 to 10.0 cm in diameter, with 8.5 cm the average size.
3. Compact, semi-upright, freely branching plant habit.
4. Uniform response in year round controlled flowering programs, forcing in 36 days on average.

5. Long lasting flowers, with flowers in a simulated home environment lasting up to two and a half weeks.
6. Medium green pubescent evergreen foliage, leathery in appearance.
7. Good foliage retention and no flower bud damage when placed in a cooler for 6 weeks with nbo lighting at 38° F.

The accompanying color photograph shows in perspective view the unique features of the new cultivar, with colors being as true as possible with color illustrations of this type.

Of the commercial cultivars known to the inventor, the most similar in comparison to Komet is the unpatented cultivar White Gish. Flower color and flower response are very much alike. Komet differs from White Gish in that Komethas ruffled petal margins and larger flowers than White Gish. Also, the flowers of Komet have dark salmon colored flecks and occasional stripes which White Gish does not. The flowers of Komet are also more heavily petaled than those of White Gish.

In the following description color references are made to The Royal Horticultural Society Colour Chart. The color values were determined on Apr. 20, 1995. All readings were taken in an office under cool white fluorescent lights, facing a west window between the hours of 10:00 a.m. and 2:00 p.m.

Classification:

*Botanical.*—*Rhododendron hybrida*, evergreen type, c.v. 'Komet'.

*Commercial.*—Florist forcing pot azalea.

INFLORESCENCE

A. Flowers (General):

*Size.*—7.0 to 10.0 cm.

*Borne.*—Terminal cluster, usually 3 per bud, ranging from 2–3.

*Form.*—Double funnel-form.

*Blooming habit.*—Once, profusely. Buds easily and uniformly in a year round program. The majority of terminal buds break color within one week of the first. Flowering begins approximately 36 days after the start of forcing.

*Fragrance.*—None.

B. Corolla (Petals):

*Texture.*—Soft.

*Substance.*—Heavy.

*Shape.*—Rounded.

*Color (fully open).*—Generally white (155D) with dark salmon flecks and occasional stripes upon opening, fading to off white color (155B) as flowers age. Upper surface: White with flecks and occasional stripes of 42B. Lower surface: White with flecks and occasional stripes of 43D. Blotch: Very diffused light green blotch (144D).

C. Bud:

*Size.*—Medium.

*Shape.*—Conoidal.

*Color.*—White (155D).

*Bud sheath.*—Immature: Light green with light brown hairs. Mature: Brown with light brown hairs.

D. Calyx:

*Form.*—Rounded.

*Color.*—144A.

E. Peduncle:

*Length.*—0.7 to 1.7 cm.

*Strength.*—Strong.

*Aspect.*—Pubescent.

F. Reproductive organs:

*Androecium (stamens).*—Number: 0 to 5; many are fully or partially petaloid. Anthers: Off White. Filaments: Length: 0.0 to 2.0 cm. Color: White.

*Gynoecium (pistils).*—Stigma: 2D. Style: Length: 1.5 to 3.0 cm. Color: 155A. Ovary: Pubescent.

PLANT CHARACTERISTICS:

A. Foliage:

*Type.*—Evergreen.

*Arrangement.*—Alternate.

*Shape.*—Elliptic.

*Size.*—Length: 2.0 to 7.0 cm. Width: 1.0 to 4.0 cm.

*Margin.*—Entire.

*Color.*—Immature: Upper Surface: Between 143A and 144A. Lower Surface: 146C. Mature: Upper surface: 147A. Lower surface: 147B. Texture: Leathery. Tomentum: Present on upper surface. Insignificant.

B. Stems:

*Color.*—Immature: 144B. Mature: 165B. Tomentum: Present, but insignificant.

C. Plant habit: Compact, semi-upright bush which achieves a uniform, symmetrical plant in a six inch pot when pinched three times. Total crop time to the dormant budded stage is 40–42 weeks to produce a plant approximately 26–34 cm in diameter and 30–36 cm in total height. Internode lengths vary widely from 2–23 mm on the same stem.

D. Branching habit: Free branching, producing 2–4 breaks when a vegetative cutting is pinched.

E. Rooting: Roots easily in 8 to 10 weeks with 75° F. soil temperature.

F. Budding ease: Plants produce flower buds easily and uniformly year round with the use of commercially available plant growth regulators. Komet has a middle natural season response time.

G. Cooler tolerance: Plants placed in a cooler as a means of breaking dormancy perform well. Komet is tolerant of six weeks in an unlighted cooler at 38° F. without foliage loss or bud damage.

H. Blooming: plants reach the stage of 12 buds showing color in 36 days on average after the cooling treatment. This varies from 22 to 39 days depending upon temperature and stage of flower bud development at the start of forcing. Komet flowers uniformly and profusely across the plants and down the sides.

I. Shelf life: When plants are moved to an office or home environment at the stage of eight open flowers, they maintain an attractive appearance for up to two weeks on average. Flowers are somewhat persistent, only occasionally dropping as flowers become old.

I claim:

1. A new and distinct cltivar of azalea plant named Komet, as described and illustrated.

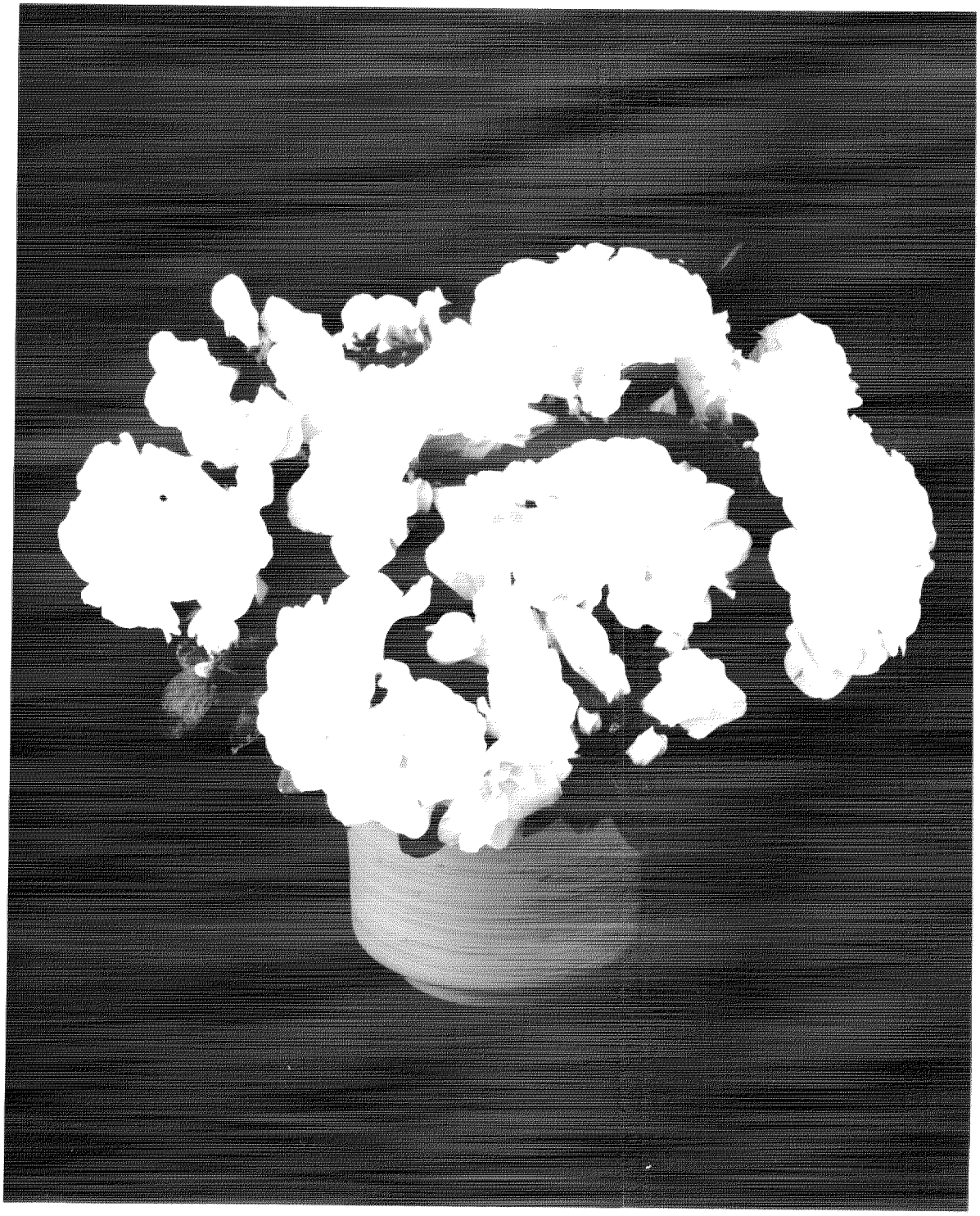

* * * * *